United States Patent [19]

Wilkinson

[11] 4,244,945
[45] Jan. 13, 1981

[54] BIOLOGICALLY ACTIVE SUBSTANCE

[75] Inventor: Samuel Wilkinson, Beckenham, England

[73] Assignee: Burroughs Wellcome Co., Research Triangle Park, N.C.

[21] Appl. No.: 30,153

[22] Filed: Apr. 16, 1979

Related U.S. Application Data

[62] Division of Ser. No. 926,795, Jul. 21, 1978, Pat. No. 4,162,307.

[30] Foreign Application Priority Data

Jul. 22, 1977 [GB] United Kingdom ............... 30909/77

[51] Int. Cl.$^3$ .................... C07C 103/52; A61K 37/00
[52] U.S. Cl. ............................. 424/177; 260/112.5 R
[58] Field of Search ................. 424/177; 260/112.5 R

[56] References Cited

PUBLICATIONS

L. Terenius, et al., Biochem. and Biophys. Res. Commun., 71, 1976, 175-179.
S. Bajusz, et al., Febs Letter, 76, 1977, 91-92.

*Primary Examiner*—Delbert R. Phillips
*Attorney, Agent, or Firm*—Donald Brown

[57] ABSTRACT

A method for the induction and/or maintenance of anaesthesia or of neuroleptanalgesia in a mammal comprising the administration to the mammal of an anaesthetic-effective or of a neuroleptanalgesic-effective, non-toxic amount of a peptide of formula H.Tyr.D-Ala.Gly.Phe.D-Leu.NHEt or a pharmacologically and pharmaceutically acceptable acid addition salt thereof.

5 Claims, No Drawings

BIOLOGICALLY ACTIVE SUBSTANCE

This is a division of application Ser. No. 926,795 filed July 21, 1978 now U.S. Pat. No. 4,162,307.

This invention relates to the medicinal use of a pentapeptide and its acid addition salts.

The present invention more particularly relates to the use of the peptide of formula (I)

H.Tyr.D-Ala.Gly.Phe.D-Leu.NHEt (I)

and its acid addition salts as anaesthetic agents and as neuroleptanalgesic agents.

The abbreviations used herein for amino acids and their radicals are those conventional in the art and may be found in, for example, *Biochemistry*, 11, 1726 (1972). In the above and throughout the following all references are to the L-amino acids and their radicals except in the case of glycine and unless otherwise stated.

The peptide of formula (I) and its acid addition salts, when assessed by a number of standard pharmacological procedures, has been found both to induce and to maintain anaesthesia in laboratory animals including rats and mice. The compounds are effective in this respect when administered by a variety of routes including parenteral, for example by intravenous or intracerebroventricular injection. Illustrative of the anaesthetic effects of the compounds are the following, which should be understood to be nonlimiting:

(i) Abolition of the righting reflex. This is characteristic of recognised anaesthetic agents such as chloral hydrate (2,2,2-trichloro-1,1-ethanediol), urethan (ethyl carbamate) and the barbiturates (derivatives of barbituric acid). An animal lacking this reflux does not roll over or attempt to regain its normal posture when placed on its back.

(ii) Abolition of the pinnal reflex. In this procedure a wire or similar probe is introduced into the ear pinna; in the normal (control) animal there is a resultant reflex twitch or shake of the affected pinna.

(iii) Abolition of the corneal reflex. In this procedure the cornea is lightly touched with a wire or similar; in the normal (control) animal there is a resultant reflex blink of the eyelids. This reflex is of clinical importance in man in that it is one of the last reflexes to be abolished during the induction of general anaesthesia.

Each of the foregoing effects (i), (ii) and (iii) may be reversed by administration of the known narcotic antagonist naloxone (1-N-allyl-7,8-dihydro-14-hydroxynormorphinone). However it has been found that morphine itself does not abolish the righting reflex in laboratory animals such as mice when administered by acute bolus injection in up to lethal doses.

In the acid addition salts of the peptide of formula (I) the activity resides in the base and the acid is of less importance although for therapeutic purposes it is preferably pharmacologically and pharmaceutically acceptable to the recipient. Examples of such suitable acids include (a) mineral acids: hydrochloric, hydrobromic, phosphoric, metaphosphoric, nitric and sulphuric acids; (b) organic acids: tartaric, acetic, citric, malic, lactic, fumaric, benzoic, glycollic, gluconic, gulonic, succinic and arylsulphonic, for example p-toluenesulphonic, acids. The pharmaceutically and pharmacologically acceptable acid addition salts together with those salts which are not so acceptable (for example salts of hydrofluoric and perchloric acids) have utility in isolation and purification of the bases, and of course the unacceptable salts are also valuable in the preparation of the acceptable salts by techniques well known in the art.

The peptide of formula (I) and its pharmacologically and pharmaceutically acceptable acid addition salts may be used in the fields of both human and veterinary medicine for the induction and/or maintenance of anaesthesia in a mammal.

The peptide or a salt thereof may be administered either alone as the sole anaesthetic agent or in combination with one or more other substances which may complement and/or supplement its activity. Such additional substances may be administered before, simultaneously with or after administration of the peptide or salt thereof and in the case of simultaneous administration the various agents may be administered either as separate doses or as a combination formulation.

As one possibility the peptide or salt thereof may be administered subsequent to administration of a benzodiazepine tranquillizer such as chlordiazepoxide (7-chloro-2-methylamino-5-phenyl-3H-1,4-benzodiazepine 4-oxide), diazepam(7-chloro-1,3-dihydro-1-methyl-5-phenyl-2H-1,4-benzodiazepin-2-one) and oxazepam(7-chloro-1,3-dihydro-3-hydroxy-5-phenyl-2H-1,4-benzodiazepin-2-one).

As another possibility the peptide or salt thereof may be administered for the maintenance of anaesthesia after this has been initially induced by the previous administration of another anaesthetic agent, for example a barbiturate such as thiopental sodium (sodium 5-ethyl-5-(1-methylbutyl)-2-thiobarbiturate).

A particular utility for the peptide of formula (I) and its pharmacologically and pharmaceutically acceptable acid addition salts, within the field of anaesthesia, is the induction and/or maintenance of the state referred to as "neuroleptanalgesia", a condition characterised by quiescence, psychic indifference to environmental stimuli, and analgesia (see, for example, Dorland's Illustrated Medical Dictionary, twenty-fifth edition, published by W. B. Saunders, 1974, at page 1041, and *"The Pharmacological Basis of Therapeutics"*, Goodman, L. S. and Gilman, A. eds., fifth edition, published by Macmillan Publishing Co. Inc., 1975, especially at Chapter 8, pages 97 to 101, all of which is incorporated herein by reference hereto). This condition is recognised by clinicians as desirable for enabling the performance of procedures such as bronchoscopy, X-ray studies, burn dressings and cystoscopy wherein a degree of patient cooperation is of value, and a fixed-dose combination comprising the narcotic analgesic fentanyl citrate (N-(1-phenethyl-4-piperidyl)propionanilide citrate) and the neuroleptic agent droperidol (1-}1-[3-(p-fluorobenzoyl)propyl]-1,2,3,6-tetrahydro-4-pyridyl}-2-benzimidazolinone) has found acceptance for use in such circumstances.

Heretofore neuroleptanalgesia has been achievable only upon administration of such a narcotic analgesic plus neuroleptic drug combination as that above mentioned. The peptide of formula (I) and its acceptable acid addition salts is thus an important clinical advance and valuable addition to the armamentarium of the medical and veterinary professions in alone enabling this result, without any additional medication being required.

In addition to its ability both to induce and to maintain anaesthesia, as hereinbefore described, the peptide of formula (I) and its acid addition salts has been found to exhibit morphine agonist activity. As generally accepted and as the term is used herein, a morphine agonist is a compound the biological activity of which mimics that of the natural alkaloid.

The pharmacological properties and therapeutic uses of morphine are well documented in the literature, see for example "The Pharmacological Basis of Therapeutics", Goodman, L. S. and Giman, A.eds., published by The MacMillan Company, New York, third edition (1965) especially at Chapter 15, pages 247 to 266, and "Martindale: The Extra Pharmacopoeia", Blacow, N. W. ed., published by The Pharmaceutical Press, London, twenty-sixth edition (1972) especially at pages 1100 to 1106, all of which is incorporated herein by reference hereto. As is well known however (Goodman, L. S. et al., loc. cit, Chapter 16) repeated administration of morphine can lead to the recipient developing an addiction to the drug and tolerance to its effects and to his manifesting withdrawal symptons when administration is discontinued. For many years therefore research has been conducted with the aim of obtaining a compound having the activity spectrum of morphine while lacking its disadvantages.

The morphine agonist properties of the peptide of formula (I) and its derivatives as hereinbefore defined include the following, which are given solely by way of illustration and should be understood to be non-limiting:

(A) In vitro:

(i) Inhibition of neurally evoked contractions of the isolated mouse was deferens when tested by the method of Hughes et al (*Brain Research*, 88 (1975) 296) (using pulses at 0.1 Hz), the inhibition being abolished by the known narcotic antagonist naloxone (1-N-allyl-7,8-dihydro-14-hydroxy normorphinone).

(ii) Reduction of electrically-induced contractions of the isolated guinea-pig ileum when prepared for stimulation after the manner of Paton (*Brit. J. Pharmacol.*, 12 (1957) 119–127). (Each intestinal segment was impaled by the anode and suspended with a 2–3 g load. Stimulus parameters: frequency: 0.1 Hz; duration: 0.4 ms; voltage (supramaximal) 30–40 V; the contractions were transduced isotonically).

(B) In vivo:

(i) The compound exhibits analgesic activity, for example it is effective in mice in the "hot plate" procedure standard in the art when tested by a modification of the method of Eddy, N. B. et al. (*J. Pharm. Exp. Therap.* 107, 385 (1953), the compound being administered by intracerebroventricular injection, and this activity is abolished by naloxone.

(ii) The compound exhibits antitussive activity, for example when tested in guinea-pigs according to the method of Boura et al, *Brit. J. Pharmacol*, 39, (1970) 225.

(iii) The compound exhibits antidiarrhoeal activity, for example it is effective in reducing castor oil-induced diarrhoea in rats.

Because of their morphine agonist activity already alluded to the peptide of formula (I) together with its pharmacologically and pharmaceutically acceptable acid addition salts may be used in the treatment of mammals in the fields of both human and veterinary medicine in any condition where an agent with a morphine-like effect is indicated. Specific utilities that may be mentioned, by way of example, include the following:

(1) The relief of pain (analgesia), for example pain arising from spasm of smooth muscle as in renal or biliary colic, pain due to terminal illness such as cancer, pain in the post-operative period, and obstetrical pain.

(2) Sedation, for example in pre-anaesthetic medication; tranquillization; the induction of sleep, especially where sleeplessness is due to pain or cough; and the relief of anxiety in general.

(3) The suppression of cough.

(4) The relief of dyspnoea, for example that of acute left ventricular failure or pulmonary oedema.

(5) The induction of constipation, for example after ileostomy or colostomy, and the treatment of diarrhoea and dysentery.

(6) The induction of euphoria and the treatment of depression, for example when allied to the relief of pain in terminal illness such as cancer.

For each of the utilities recited hereinbefore for the peptide of formula (I) and its acid addition salts, that is to say, whether for use for the induction and/or maintenance of anaesthesia (for example the induction and/or maintenance of neuroleptanalgesia) or for use in a condition where an agent with a morphine-like effect is indicated (for example the utilities specifically indentified hereinbefore under (1), (2), (3), (4), (5) or (6)) the amount required of the peptide or acid addition salt thereof (hereafter referred to as the active ingredient) will vary with the route of administration and with the nature and required extent of the desired effect, and will ultimately be at the discretion of the physician or veterinarian. In general however for each of these utilities the dosage will be in the range 0.0025 $\mu$g to 40 mg per kilogram bodyweight of mammal, preferably 0.0025 $\mu$g to 10.0 mg/kg, more preferably 0.01 $\mu$g to 4.0 mg/kg and optimally 0.25 to 400 $\mu$g/kg (all dosages calculated with reference to the peptide base).

The active ingredient may be administered by any route appropriate to the effect to be achieved, suitable routes including oral, rectal, nasal, topical (buccal), vaginal and parenteral (including subcutaneous, intramuscular and intravenous). It will be appreciated that the preferred route will vary with the effect to be achieved and thus for example in the relief of obstetrical pain administration directly into the spinal cord may be advantageous.

While it is possible for the active ingredient to be administered as the raw chemical it is preferable to present it as a pharmaceutical formulation preparation.

The formulations, both veterinary and for human use, of the present invention comprise an active ingredient, as above defined, together with one or more acceptable carriers therefor and optionally other therapeutic ingredients. The carrier(s) must be "acceptable" in the sense of being compatible with the other ingredients of the formulation and not deleterious to the recipient thereof. Desirably the formulations should not include oxidising agents and other substances with which peptides are known to be incompatible.

The formulations include those suitable for oral, rectal, nasal, topical (buccal), vaginal or parenteral (including subcutaneous, intramuscular and intravenous) administration, although the most suitable route in any given case will depend upon for example the active ingredient and the condition to be treated. The formulations may conveniently be presented in unit dosage form and may be prepared by any of the methods well known in the art of pharmacy. All methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product into the desired formulation.

Formulations of the present invention suitable for oral administration may be presented as discrete units such as capsules, cachets or tablets each containing a predetermined amount of the active ingredient; as a powder or granules; or as a solution or a suspension in an aqueous liquid or a non-aqueous liquid; or an an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine, the active ingredient in a free-flowing form such as a powder or granules, optionally mixed with a binder, lubricant, inert diluent, lubricating, surface active or dispersing agent. Moulded tablets may be made by moulding in a suitable machine, a mixture of the powdered compound moistened with an inert liquid diluent.

Formulations for rectal administration may be presented as a suppository with the usual carriers such as cocoa butter, while a suitable formulation for nasal administration is nasal drops comprising the active ingredient in aqueous or oily solution.

Formulations suitable for topical administration in the mouth include lozenges comprising the active ingredient in a flavoured basis, usually sucrose and acacia or tragacanth; and pastilles comprising the active ingredient in an inert basis such as gelatin and glycerin, or sucrose and acacia.

Formulations suitable for vaginal administration may be presented as pessaries, creams, pastes or spray formulations containing in addition to the active ingredient such carriers as are known in the art to be appropriate.

Formulations suitable for parenteral administration conveniently comprise sterile aqueous solutions of the active ingredient, which solutions are preferably isotonic with the blood of the recipient. Such formulations may be conveniently prepared by dissolving solid active ingredient in water to produce an aqueous solution, and rendering said solution sterile and isotonic with the blood of the recipient. The formulations may be presented in unit—or in multi-dose containers, for example sealed ampoules or vials.

Formulations suitable for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose.

It should be understood that in addition to the aforementioned ingredients the formulations of this invention may include one or more additional ingredients such as diluents, buffers, flavouring agents, binders, surface active agents, thickeners, lubricants, preservatives (including anti-oxidants) and the like.

Where the formulation, for human or for veterinary use, is presented in unit dosage form, for example those unit dosage forms specifically mentioned above, each unit thereof conveniently contains the active ingredient (as above defined) in an amount in the range 0.125 g. to 2 g., preferably 1.25 g. to 200 mg. and optimally 12.5 g. to 20 mg. (all weights calculated with reference to the peptide base).

The peptide of formula (I) and its acid addition salts may be prepared by any of the methods known in the art for the preparation of compounds of analogous structure. Thus they may be formed by the sequential coupling of appropriate amino acids using either classical methods of peptide synthesis or solid phase procedures, or by the initial preparation and subsequent coupling of peptide subunits.

Such reactions may be effected by, for example, activating the carboxylic acid group of the ingoing amino acid and protecting the non-reacting amino and carboxylic acid groups. Such techniques are standard in the peptide art. Details of suitable activating and protecting (masking) groups and of suitable reaction conditions (both for the coupling reactions and for the removal of protecting groups) giving the minimum of racemisation may be found in the following literature, all of which is incorporated herein by reference hereto, which is given purely by way of exemplification and which is intended to be neither exhaustive nor limiting.

Schröder and Lüebke, "The Peptides" (Academic Press) (1965).

Bellean and Malek, *J. Am. Chem. Soc.*, 90, 165 (1968).

Tilak, *Tetrahedron Letters*, 849 (1970).

Beyerman, *Helv. Chim. Acta.*, 56, 1729 (1973).

Stewart and Young, "*Solid Phase Peptide Synthesis*" (W. H. Freeman and Co.) (1969).

Depending upon the reaction conditions the peptide of formula (I) is obtained in the form of the free base or as an acid addition salt thereof. The acid addition salts may be converted into the free bases or salts of other acids, and the bases may be converted into acid addition salts thereof, by techniques well known in the art.

The peptide of formula (I) and acid addition salts thereof may thus be prepared by condensing a reagent (II)

$$H-Y^1-OH \quad (II)$$

wherein $Y^1$ is selected from the radical —Tyr— and a partial radical sequence having the radical —Tyr— at its N-terminal end and from thereon corresponding to formula (I), with a reagent (III)

$$H-Y^2 \quad (III)$$

wherein $Y^2$ corresponds to the balance of the above defined product, the reagents (II) and (III) being optionally protected and/or activated where and as appropriate; followed if necessary and as appropriate by one or both of the steps of deprotection of the product and conversion of the product into the base or an acid addition salt thereof.

It will be appreciated that the peptide of formula (I) may also be prepared by reaction of a corresponding peptide alkyl ester, for example the methyl ester, with an appropriate monoalkylamine.

It will be appreciated from the foregoing that what we will claim may comprise any novel feature described herein, principally and not exclusively, for example:

(a) A method for the induction and/or maintenance of anaesthesia in a mammal, comprising the administration to the mammal of an anaesthetic-effective, non-toxic amount of the peptide of formula (I) or a pharmacologically and pharmaceutically acceptable acid addition salt thereof.

(b) A method for the induction and/or maintenance of neuroleptanalgesia in a mammal, comprising the administration to the mammal of a neuroleptanalgesic-effective, non-toxic amount of the peptide of formula (I) or a pharmacologically and pharmaceutically acceptable acid addition salt thereof.

The following Examples serve to illustrate the present invention but should not be construed as in any way providing a limitation thereof. All temperatures are in degrees Celsius.

EXPERIMENTAL SECTION

The following abbreviations are used throughout
HOBT: 1-hydroxybenzotriazole
DCCI: dicyclohexylcarbodiimide
DCU: dicyclohexylurea
NMM: N-methylmorpholine
DMF: dimethylformamide
Pr: isopropanol
Pr$_2$O: diisopropyl ether
po: petroleum ether
EtOAc: ethyl acetate
Z: benzyloxycarbonyl
Bu: tertiary butyl
BOC: tertiary butyloxycarbonyl
Bzl: benzyl Peptides were examined by tlc on Merck silicagel plates with the following solvent systems:
(1) methylethylketone
(2) n-butanol: acetic acid: water (3:1:1)
(3) chloroform: methanol: 32% acetic acid (12:9:4)
(4) chloroform: methanol: 0.880 ammonia (12:9:4)
(5) ethylacetate: n-butanol: acetic acid: water (1:1:1:1)
(6) chloroform: methanol (8:1)

All amino acids were of the L-configuration unless otherwise stated.

Optical rotations were determined on a Bendix NPL automatic polarimeter.

The amino acid compositions of peptide hydrolysates (6 N.HCl at 110° for 24 hours in evacuated sealed tubes) were determined with a Beckman-Spinco Model 120 C amino acid analyser or with a Rank Chromostak amino acid analyser.

The following general procedures were used throughout the syntheses of the peptides.
(a) Couplings were carried out in DMF and were mediated by DCCI.
(b) Amino acid ester hydrochlorides were converted to the free esters by addition of the tertiary base, either triethylamine or N-methyl morpholine.
(c) HOBT was added at the coupling stage when fragment condensation involved a peptide having an optically active carboxy terminal amino acid e.g. coupling with BOC.Tyr.D-Ala.Gly.Phe.OH.
(d) Couplings were allowed to proceed for 24 hours in the cold room at +4° C.
(e) After coupling, purification was effected by washing with acid and base to remove unchanged reactants.
(f) Alkaline saponifications were carried out in aqueous methanol with an autotitrator at pH 11.5 to 12.0 with N.NaOH.
(g) Benzyloxycarbonyl protecting groups were removed by hydrogenolysis in methanol/acetic acid with 10% palladium on charcoal.
(h) The resulting acetate salts from the above hydrogenolysis were converted to the corresponding hydrochlorides by an addition of methanolic hydrogen chloride.
(i) Benzyl protecting groups were removed by hydrogenolysis in methanol with 10% palladium on charcoal.
(j) Tertiary butyl and tertiary butyloxycarbonyl protecting groups were removed with N-hydrogen chloride in acetic acid, in the presence of anisole to act as a scavenger. Cleavage was allowed to proceed for 60 to 90 minutes.

OBu protecting groups on the alcoholic functions of threonine and serine were removed with trifluoroacetic acid containing 10% water, cleavage being allowed to proceed for 90 minutes.

EXAMPLE 1

Preparation of H.Tyr.D-Ala.Gly.Phe.D-Leu.NHEt hydrochloride

H.Tyr.D-Ala.Gly.Phe.D-Leu.NHEt hydrochloride was prepared according to the scheme set out in Table 1. After purification on carboxymethyl cellulose the end-product peptide (as the acetate addition salt) was dissolved in water. Subsequently one equivalent of 1 M hydrochloric acid was added and the resultant hydrochloride obtained by freeze-drying the solution.

The hydrochloride had the following characterising data by thin layer chromatography (Merck silica gel plates and the solvent systems indicated)

Rf = 0.61$^2$; 0.93$^4$; 0.61$^5$ and had an optical rotation of $[\alpha]_D^{25} = +46.5°$ (c = 0.5 in methanol)

TABLE 1

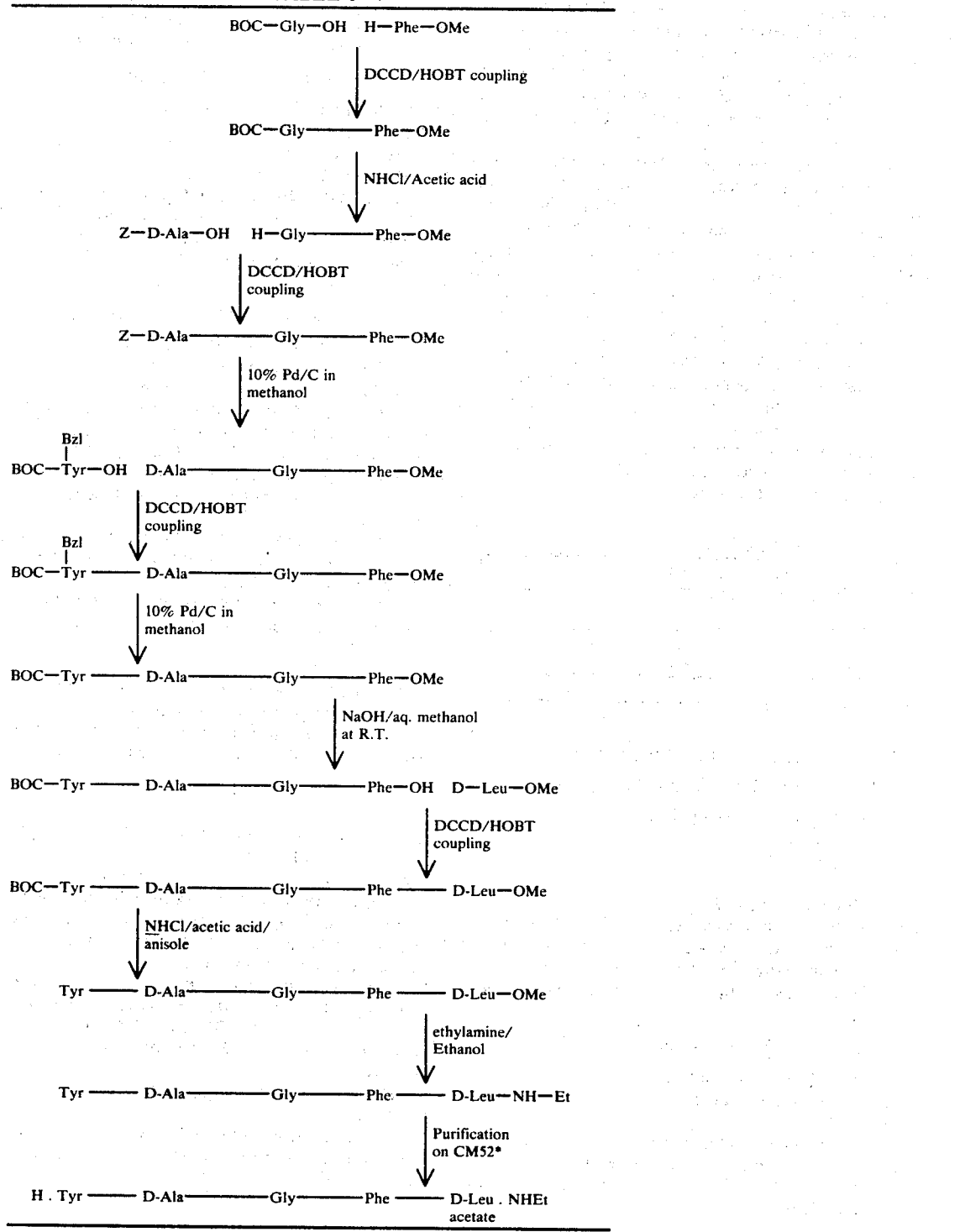

*CM52 is the Whatman brand of carboxy methyl cellulose - peptides are eluted in order of basicity by an ammonium acetate concentration gradient.

EXAMPLE 2: Pharmacological Activity

H.Tyr.D-Ala.Gly.Phe.D-Leu.NHEt hydrochloride was tested for the following activities according to standard pharmacological procedures.

(A) Analgesia in mice in the hot plate test (modification of the method of Eddy, N. B. et al., *J. Pharm. Exp. Therap.* (1953) 107, 385, the peptide being administered by intracerebroventricular injection).

(B) Antidiarrhoeal activity in the rat. In this procedure rats were starved for 24 hours, the peptide then administered either subcutaneously or orally followed after 15 minutes by 1 ml castor oil per rat given orally.

(C) For antitussive testing, guinea-pigs are subjected to an aerosol containing 20% citric acid, 30 minutes after administration of compound (orally or subcutaneously). The number of coughs during a five minute exposure are counted and meaned for six animals per treatment. The method is that described by Boura, A. L. A., Green, A. F. and Saunders, I. A. Br. J. Pharmac., May 1970, Vol. 39, No. 1, page 225.

(D) Compounds are tested for anaesthetic effects following intracerebroventricular injection in mice. The animals are observed for loss of righting reflex (failure to roll over within 10 seconds of being turned on their backs), loss of pinnal reflex (failure to flick the ear in response to a light touch at the base of the pinna) and loss of corneal reflux (failure to blink when the cornea is touched lightly). Loss of all three reflexes constitutes anaesthesia. In addition, any other effects are noted. If a compound shows a degree of anaesthesia at the starting dose of 10 μg/mouse, further doses are done and and ED50 calculated. Interesting compounds are then tested intravenously in the same manner.

From the data obtained the respective ED50 figures were calculated (i.e. the dose required to elicit the appropriate effect in 50% of the animals). N.T.: not tested.

TABLE 1

| Results expressed as ED50 for H . Tyr . D-Ala . Gly . Phe . D-Leu . NHET . hydrochloride | | | | |
|---|---|---|---|---|
| Mouse hot plate μg/ mouse - i.c.v. -ANALESIA | Anti- diarrhoea mg/kg (rat) s.c. | Anti-tussive mg/kg - guinea-pig | Anaesthesia mg/kg i.v. | Anaesthesia μg/mouse i.c.v. |
| 0.03 | 10 | 2.0 | 20 | 2.8 |

EXAMPLE 3: Pharmaceutical Formulations (A) Tablet Formulation (20 mg/tablet)

Compound of formula (I): 20 mg
Lactose: 76 mg
Maize Starch: 10 mg
Gelatin: 2 mg
Magnesium Stearate: 2 mg Mix together the compound of formula (I), Lactose and Maize Starch. Granulate with a solution of the Gelatin dissolved in water. Dry the granules, add the Magnesium Stearate and compress to produce tablets, 110 mg per tablet.

(B) Suppository (5 mg/product)

Compound of formula (I): 250 mg
Suppository Base (Massa
Esterinum (C): to 100 mg Melt the suppository base at 40° C. Gradually incorporate the compound of formula (I) in fine powder form and mix until homogeneous. Pour into suitable moulds, 2 g per mould, and allow to set.

Massa Esterinum C is a commercially available suppository base consisting of a mixture of mono, di, and triglycerides of saturated vegetable fatty acids. It is marketed by Henkel International, Dusseldorf.

(C) Pessary (5 mg/product)

Compound of formula (I): 5 mg
Lactose: 400 mg
Providone: 5 mg
Magnesium Stearate: 5 mg Mix together the compound of formula (I) and Lactose. Granulate with a solution of Povidone in 50% aqueous ethanol. Dry the granules add the Magnesium Stearate and compress on suitably shaped punches, 415 mg per pessary.

(D) Freeze-dried Injection 100 mg/vial

Compound of formula (I): 100 mg
Water for Injections to: 2.0 ml

Dissolve the compound of formula (I) in the Water for Injections. Sterilise the solution by passage through a membrane filter, 0.2 μm pore size, collecting the filtrate in a sterile receiver. Fill into sterile glass vials, 2 ml/vial under aseptic conditions and freeze-dry. Close the vials with sterile rubber closures secured with an aluminium seal.

The injection is reconstructed prior to administration by the addition of a convenient volume of Water for Injections or sterile saline solution.

In the foregoing, the weight of the compound of formula (I) is in each instance calculated with reference to the peptide base.

What we claim is:

1. A method for the induction and/or maintenance of neuroleptanalgesia in a mammal, comprising the administration to the mammal of a neuroleptanalgesic-effective, non-toxic amount of a peptide of formula H.Tyr.D-Ala.Gly.Phe.D-Leu.NHEt or a pharmacologically and pharmaceutically acceptable acid addition salt thereof.

2. A method according to claim 1 wherein a pharmaceutical formulation comprising the peptide or acid addition salt thereof together with a pharmaceutically and pharmacologically acceptable carrier therefor is administered to the mammal.

3. A method according to claim 1 wherein the peptide or acid addition salt thereof is administered at a dosage in the range of from 0.0025 μg to 40 mg per kilogramme bodyweight of the mammal, calculated as the base.

4. A method according to claim 1 wherein the mammal is man.

5. The method of claim 1 in which the peptide or salt thereof is administered with a pharmaceutically acceptable carrier therefore.

* * * * *